United States Patent [19]
Willoughby

[11] Patent Number: 4,968,885
[45] Date of Patent: Nov. 6, 1990

[54] METHOD AND APPARATUS FOR INTRODUCTION OF LIQUID EFFLUENT INTO MASS SPECTROMETER AND OTHER GAS-PHASE OR PARTICLE DETECTORS

[75] Inventor: Ross C. Willoughby, Pittsburgh, Pa.

[73] Assignee: Extrel Corporation, Pittsburgh, Pa.

[21] Appl. No.: 393,846

[22] Filed: Aug. 14, 1989

Related U.S. Application Data

[63] Continuation of Ser. No. 22,725, Mar. 6, 1987, abandoned.

[51] Int. Cl.$^5$ ............................................. H01J 49/04
[52] U.S. Cl. .................................... 250/288; 250/283; 73/863.11; 73/863.12; 73/864.81
[58] Field of Search .................. 250/288 A, 288, 283; 73/863.11, 863.12, 864.81

[56] References Cited

U.S. PATENT DOCUMENTS

| | | | |
|---|---|---|---|
| 3,997,298 | 12/1976 | McLafferty et al. | 250/288 A |
| 4,160,161 | 7/1979 | Horton | 250/283 |
| 4,298,795 | 11/1981 | Takeuchi et al. | 250/282 |
| 4,358,302 | 11/1982 | Dahneke | 250/288 |
| 4,383,171 | 5/1983 | Sinha et al. | 250/288 |
| 4,531,056 | 7/1985 | Labowsky et al. | 250/288 A |
| 4,607,163 | 8/1986 | Mizuno | 250/288 A |
| 4,687,929 | 8/1987 | Browner et al. | 250/288 A |
| 4,730,111 | 3/1988 | Vestal et al. | 250/288 A |

OTHER PUBLICATIONS

Kerker (1975), Advances in Colloid and Interface Science, 5, 105 entitled "Laboratory Generation of Aerosols".
Gretzinger and Marshall (1961), A. I. Ch. E. Journal, 2(2), 312, entitled "Characteristics of Pneumatic Atomization".
Willoughby (1983), "Studies with an Aerosol Generation Interface for Liquid Chromatography with Mass Spectrometry", PhD Thesis, Georgia Institute of Technology.

Primary Examiner—Jack I. Berman
Attorney, Agent, or Firm—Penrose Lucas Albright

[57] ABSTRACT

Methods and apparatus for liquid sample introduction into chemical detectors that require the sample to be transformed from a flowing stream into either gaseous or particulate states. The effluent from either a process stream or a liquid chromatograph is nebulized by combined thermal and penumatic processes within an inner fused silicon capillary tube heated by conduction through a relatively conductive sheathing gas such as helium or hydrogen from a surrounding electrical resistance heated outer capillary tube composed of a pure metal having a comparatively high linear relationship between temperature and electrical resistance to provide a uniform conduction of heat energy to the inner tube to form a well-collimated, partially or completely desolvated aerosol, with the less volatile solute components of the sample stream remaining in the particulate state. An expansion chamber at atmospheric pressure or less pressure slows the sheathing gas which surrounds the solvent vapor and solute particles sufficiently to form a stream which carries the solute particles in a manner that they avoid impacting the walls of the expansion chamber. The gaseous components of the aerosol are then separated from the solvent-depleted solute particles using either cryotrapping or momentum separation. The enriched solute particles are vaporized, ionized, and/or detected by suitable gas-phase or particle detectors. The device is primarily an interface between the liquid chromatograph or process streams and the mass spectrometer.

49 Claims, 6 Drawing Sheets

METHOD AND APPARATUS FOR INTRODUCTION OF LIQUID EFFLUENT INTO MASS SPECTROMETER AND OTHER GAS-PHASE OR PARTICLE DETECTORS

This is a continuation of application Ser. No. 022,725, filed Mar. 6, 1987, now abandoned.

BACKGROUND OF THE INVENTION

Successful liquid sample introduction into gas-phase or particle detectors is dependent upon the interface between the liquid stream and the detector. The coexistence of continuous liquid sample introduction and normal operating requirements of the gas-phase detectors present compatability problems, Difficulties are sometimes encountered in accommodating the mass flow from the liquid stream into the detector. In addition, degradation of thermally labile sample components may occur during the evaporation processes prior to gas-phase detection. In the case of gas-phase detectors such as mass spectrometers, where detection occurs at a reduced pressures, vacuum locks and pumping requirements may be considerations. General requirements for interfaces between liquid streams and gas-phase detectors are: (1) The sample must be evaporated prior to detection; (2) Minimal thermal degradation should occur during the sample evaporation process; (3) The sample transport efficiency should be sufficiently high so that adequate sensitivity is observed; (4) The normal operating conditions of the detector should be maintained during sample introduction; and (5) The sample's composition should be maintained while being transported to and through the interface (e.g. minimal chromatographic band broadening). Success in interfacing liquid streams to gas-phase detectors depends on how well the foregoing requirements are met.

The principal application of the present device to gas-phase detection of liquid streams is the introduction of the effluent from a liquid chromatograph into a mass spectrometer. The interfacing between liquid chromatography (LC) and mass spectrometry (MS) is referred to as LC-MS. Although the present invention relates to the general field of liquid sample introduction into gas-phase or particle detectors, most prior work in this area has concentrated on LC-MS because it has presented formidable obstacles to interface design. This background discussion therefore focuses on LC-MS.

Complex gas-phase detectors, mass spectrometers, detect gas-phase ions formed by a variety of mechanisms; electron impact (EI) ionization and chemical ionization (CI) are the most commonly practiced approaches. With EI ionization, the sample gas at $10^{-3}$ – $10^{-6}$ torr is bombarded with electrons of sufficient energy (generally 70 eV) to excite electronic energy levels of sample molecules beyond the ionization potential so that a electron is removed from the sample molecule, making it a positive ion. Upon sample ion formation in the EI mode, excess energy imparted to the sample molecule from the bombarding electron causes bond cleavage or fragmentation. It is a characteristic and reproducible nature of EI fragmentation, indicative of molecular structure, that provides this technique with broad utility for the analysis of samples with an unknown composition. In contrast, the CI mode operates at higher pressures relative to EI (typically at one torr), whereby the ionization occurs due to collision of sample molecules with reagent gas ions. The analytical utility of CI is generally found in the presence of molecular weight information. With CI, the limited and irreproducible fragmentation of sample molecules is essentially of no value. It should be stressed that the ionization process ultimately determines the qualitative information obtained with the mass spectrometer. Alternative ionization techniques are atmospheric pressure ionization (API) at 760 torr and field ionization at $10^{-4}$ torr. It is preferable to use a variety of ionization techniques, including EI and CI, to obtain the maximum information for a given sample. LC-MS techniques that place a restriction upon ionization conditions also are limited in the sample information obtained for a given analysis.

Mass spectra of many compounds, usually those ionized under EI conditions, have been compiled in massive computerized data-base libraries for subsequent comparison with acquired spectra (fragment ions) from samples of unknown composition. It would be therefore a significant advantage for LC-MS devices to make use of such spectral libraries because computer comparisons can be made in a matter of seconds. Hence, for the wide use there is a need for LC-MS devices that utilize EI ionization modes. Unfortunately, only few prior art devices are reported to have the capability of producing EI spectra of thermally labile and/or involatile compounds.

Effluent from either a liquid chromatograph or a liquid process stream must be accommodated by the mass spectrometer interfacing techniques. The pressure requirements for ionization, as discussed, are dependent upon the mode of ionization, and limited by the mass flow into the ionization region of the mass spectrometer and the pumping capacity of the mass spectrometer. The evaporation of liquid flowing at 1–2 mL/min may produce as much as a liter per minute of gaseous sample at STP (Standard Temperature and Pressure), which amounts to $10^8$ liters per minute of gas at $10^{-5}$ torr (i.e. EI conditions), far exceeding the pumping capabilities of conventional mass spectrometers. Ionization techniques which occur at pressures of one millitorr or higher, such as CI, require less pumping but usually result in significant ion-molecule reaction chemistry which yields little structural fragmentation information. Due to the requirement of low pressure for EI ionization, direct introduction of a continuous stream of liquid from a liquid chromatograph is difficult to attain without extremely large capacity pumping systems such as cryogenic pumping.

The evaporation or desorption process, whereby the sample is transformed into gas, may also result in thermal degradation (pyrolysis), reactions, or rearrangements of the original sample molecules. These sample losses are most prevalent with sample components that are thermally labile and/or involatile, commonly separated by liquid chromatography. Mass analysis of these thermally labile and/or involatile molecules is usually limited by the inability to produce intact gas-phase ions of these species. Therefore, it is important in development of interfaces between the LC and MS to vaporize the sample with minimal degradation or loss of analyte.

There have been a variety of approaches to interfacing the LC with the MS and this work has been extensively reviewed (1,2,3,4). The common objective of all interfacing techniques is efficiency in the production of gas-phase sample ions.

Direct Liquid Introduction (DLI) is one of the simplest approaches to interfacing LC with MS. With DLI, the effluent from a liquid chromatograph flows through a tiny circular aperture or tube with a diameter on the order of three to ten micrometers. A high velocity cylindrical liquid jet is directed into the ionization chamber. There have been a wide variety of designs using this approach and they all have the same basic configuration (reviewed in 5 and 6). The jet may proceed through a heated desolvation region before entering the ionization region to aid in solvent evaporation. This technique typically has been limited to micro-bore LC flow rates, less than one hundred microliters per minute. To accommodate direct introduction of liquid into ion source, cryogenic pumping has been used to trap the excess sample onto a cold surface of the outside of the ion source. In cases where normal LC flow rates are used, 1-2 mL/min, the effluent has been split, leaving only a fraction of the sample to be sampled into the mass spectrometer. Another limitation of the DLI technique is that the spectra produced yield only CI data. Little or no structural information is thus obtained, in contrast to EI. In addition, more costly differential pumping is required to maintain the mass analyzer pressures sufficiently low. In practice DLI has been plagued by repeated clogging of the micron sized orifices, causing the approach to be cumbersome, with significant downtime. The alignment and the instability of micron sized liquid jets also make DLI experimentally difficult in that data acquired may be noisy and irreproducible. However, the advantage of this technique is the lack of thermal degradation when analyzing thermally labile compounds. Further discussion of this technique may be found in U.S. Pat. No. 3,997,298 of Dec. 14, 1976 and U.S. Pat. No. 4,403,147 of Sept. 6, 1983.

Mechanical Transport (MT) is an LC-MS approach whereby the effluent from the LC is deposited on a moving surface, such as a wire or belt. Heat may be applied to the sample to remove solvent and the desolvated sample is mechanically transported on the wire or belt through a series of vacuum locks into the low pressure ion source of the mass spectrometer. Both EI and CI mass spectra have been obtained with this technique. A limitation of this technique is the requirement that the sample be evaporated or desorbed from the moving surface prior to ionization. Thermal degradation may occur during the thermal evaporation process. Operation of mechanical transport devices is frequently cumbersome due to design complexity and jamming of moving parts. The chromatographic profile of sample may be degraded by the non-uniform application of sample upon the moving surface. This approach is explained in greater depth in U.S. Pat. No. 4,055,987 of Nov. 1, 1977.

Thermospray (TSY) is a more widely used approach to LC-MS. The effluent from the LC flows through a thermal vaporizer into a heated vaporizer chamber in the ion source region of the MS. The thermal vaporizer transforms the sample into an ion-vapor plasma in a vaporizer chamber. A small fraction of the ion-vapor is sampled into the ion optics region of the mass spectrometer through a small aperture. The efficiency of sampling analyte through the sampling aperture is quite low. The majority of the ion-vapor is evacuated through a roughing line connected to the vaporizer chamber. As with DLI, costly differential pumping between the ion optics region and the mass analyzer region is required to maintain an adequate vacuum. The vaporization process produces gas-phase reagent ions when buffered solutions, such as aqueous ammonium acetate, are pumped through the thermal vaporizer. This ionization process, known as thermospray ionization, produces CI-like spectra. Under normal operational conditions, thermal degradation has been observed with the use of the thermal vaporizer; however, a large number of thermally labile compounds have been analyzed with this technique with minimal degradation. TSY has several limitations, most notably is the lack of structural information such as that obtained under EI ionization conditions. The response of various compounds depends upon the chemical nature of the substance being analysed. Consequently, it is sometimes difficult to predict response for poorly characterized samples. Thermospray processes are described in further detail in Canadian Patent No. 1,162,331 of Feb. 14, 1984, and U.S. application Ser. No. 527,751, filed Aug. 30, 1985, and a continuation thereof filed Ser. No. 832,743, issued as U.S. Pat. No. 4,730,111, to M. Vestal and C. Blakely on Mar. 8, 1988.

Monodispersed Aerosol Generation Interface for Combining liquid chromatography with mass spectrometry (MAGIC) is an approach to LC-MS whereby effluent is pumped through a tiny orifice or tube, forming a stable liquid jet. The liquid jet breaks up into uniformly sized or monodispersed droplets. The droplets are dispersed in a near-atmospheric pressure desolvation chamber with a dispersion gas that serves to prevent coagulation of the droplets as well as conduct thermal energy to the droplets resulting in rapid desolvation. This approach requires a large diameter desolvation chamber at near atmospheric pressure to allow efficient desolvation. The effect of lowering desolvation chamber pressure on the rate of solvent evaporation has theoretically been treated by Fuchs and Sutugen (16). The rate of evaporation of a liquid droplet is significantly reduced with decreases in pressure. In the absence of dispersion gas, the droplets receive insufficient thermal energy which prevents their complete desolvation. Dispersion gas flows of greater than one liter per minute have been used in order to maintain sufficiently high pressure in the desolvation chamber. Subsequent to desolvation, solvent-depleted solute particles are accelerated through a nozzle into a vacuum chamber to form a high velocity aerosol beam. The lighter solvent vapor and dispersion gas, compared to the more massive solute particles, expand outward from the axis of the aerosol beam, leaving a collimated particle beam devoid of gaseous components. The gaseous components of the aerosol beam are removed in a two-stage pressure reduction process, accomplished by directing the particle beam through two successive skimmers that separate two successively lower pressure vacuum chambers. The solute particle beam proceeds through the skimmers into the ion source region where enriched solute is thermally desorbed from surfaces in the ion source region and ionized by a conventional CI or EI ionization process.

The MAGIC approach to LC-MS has the advantage of ionizing solute under EI conditions. However, the requirement of near atmospheric pressure desolvation significantly reduces the solute transport efficiency into the low pressure ion source of the mass spectrometer. The addition of high flow rates of dispersion gas creates turbulence at the nozzles and significant loss in transport efficiency is observed due to impact on the surfaces of the skimmers and nozzles as well as walls of the desolvation chamber. The requisite high gas lead also tends to increase the solid angle expansion of the particle beam and to favor the use of a less efficient two-stage separator device. Because of these conditions, transport efficiency of solute into the ion source is generally on the order of five percent. With MAGIC, the mobile phase composition does not affect the response for various analytes as does the thermospray technique which in some cases requires mobile phase additives for sensitive response. Also, no differential pumping is required with this technique when EI ionization is the only mode employed. Additional details on this technique are presented in U.S. patent application Ser. No. 623,711 filed June 22, 1984, by R. Browner and R. Willoughby, which issued Dec. 16, 1986 as U.S. Pat. No. 4,629,478, and in a continuation thereof.

MAGIC can be considered a particle beam introduction technique. For this discussion, particle beam introduction is considered as a technique of accelerating an aerosol through a nozzle into successive vacuum chambers while skimming the aerosol particles on axis, forming a particle beam, and pumping away gaseous components of the aerosol beam off-axis. The result of this process is the efficient separation of aerosol particles from gaseous material, with the particles being transported more efficiently into lower pressure regions because of the higher momentum of the particle when compared to the gas molecules. Prior particle beam introduction techniques for mass spectrometry have applied to two areas: (1) Real-time aerosol monitoring (7-9); and (2) Liquid sample introduction where an aerosol generation step precedes the particle beam introduction (10-14). The MAGIC technique is an example of the latter. The present invention also includes a particle beam solute enrichment step when applied to sample introduction into the mass spectrometer.

Performance of particle beam introduction techniques is dependent upon the properties of the aerosol. The solid angle dispersion of the particle beam is dependent upon the size of the solute particles, the pressure from the aerosol source, and the geometry of the nozzle. Israel and Friedlander (15) experimentally showed the relationships of these parameters on particle beam dispersion. Their results show: (1) Particle beam angular dispersion increases with aerosol source pressure: (2) Particle beam angular dispersion decreases with increase in particle size: and (3) Particle beam expansion is more uniform with changes in particle size when capillary versus converging nozzles are used. Therefore, the nature of the aerosol generation process in terms of gas flow and pressure, and particle size and distributionultimately determines the efficiency of the particle beam introduction technique.

A variety of aerosol generators have been used with the particle beam approach to liquid sample introduction into the mass spectrometer. These include the Berglund-Liu monodisperse aerosol generator (8,10-14), the Willoughby-Browner monodisperse aerosol generator (14), and DeVilbiss and ultrasonic nebulizer (10-13). A major limitation of prior particle beam techniques was the difficulty in desolvation of the aerosol droplets subsequent to aerosol generation. Prior techniques required a desolvation chamber or increased gas load to remove solvent from the droplets. The generation of droplets greater than about ten microns in diameter with prior aerosol generation techniques leads to greater likelihood of particle losses in the desolvation chambers and nozzles due to impaction or settling process. The aerosol generation process of the present invention is designed to permit precise control over aerosol properties, including the droplet size, direction, and rate of evaporation. With enhanced control over the aerosol generation and desolvation processes, the efficiency of the particle transport to various detectors is increased.

The solid angle dispersion of particle beams has been shown to increase with increases in aerosol source pressure (15). Thus, the prior particle beam techniques that require high gas loads for aerosol generation or desolvation tend to have more divergent particle beams. This requires that only part of the particle beam cross-section can be sampled through axial skimmers because pressures in subsequent chambers exceed the upper pressure limitation of the detector. Thus, the entire cross-section of a less divergent particle beam could in theory be collected with the same skimmer diameter while maintaining the same detector pressure. The result of a less divergent particle beam is more efficient sample transport to the detector. Consequently, an objective of the present device is to decrease the gas load from the aerosol generation process to enhance sample transport efficiency.

The use of particle beam techniques for sample introduction into the mass spectrometer has demonstrated the ability to produce spectra under electron impact ionization conditions (7-14). A major objective of the present device is to enhance the ability to volatilize the particles once the particle beam enters the ion source region of the mass spectrometer. The objective is to form intact gas-phase molecular species of substances originating in the particle. But prior particle beam sample introduction devices have experienced difficulty in forming intact molecular ions due to thermal fragmentation of molecules during evaporation from heated surfaces (8). Particle volatilization process depends upon the equilibrium surface vapor pressure of molecules originating from the particles, the temperature and material of the particle beam collection surface, and the presence of other components in the particle matrix. Control of these factors is essential to the performance of the present device.

Other applications of liquid sample introduction into gas-phase or particle detectors have been reported for light scattering (17), flame ionization (18), atomic absorption or emission spectrophotometry (19). The enhanced control of aerosol generation, desolvation and solute enrichment with the present device is applicable to a variety of detectors.

Sources for the above mentioned in the above background history are:

1. P. J. Arpino, J. Chormatogr. 323, 3 (1985).
2. D. E. Games, Adv. Chomatogr. 21, 1 (1983).
3. C. G. Edmonds, J. A. McCloskey, V. A. Edmonds, Biomed Mass Spectrom. 10, 237 (1983).
4. R. C. Willoughby, R. F. Browner, Trace Analysis. Vol 2, p. 69, ed. J. F. Lawrence, Academic Press (1982).
5. W. M. A. Niessen, Chromatographia, 21, 5 (1986).
6. W. M. A. Niessen, Chromatographia, 21, 5 (1986).
7. J. J. Stoffels, "A Direct Air-Sampling Inlet for Surface Ionization Mass Spectrometry of Airborne Particles," presented at the 24th Annual Meeting of ASMS, San Diego, Calif. 1976.
8. M. P. Sinha, C. E. Griffin, D. D. Norris, and S. K. Friedlander, "Analysis of Aerosol Particles by Mass Spectrometry," presented at the 28th Annual Meeting of ASMS, New York, N.Y. 1980.

9. J. Allen and R. K. Gould, Rev. Sci. Instum. 52 (6), June 1981.
10. F. T. Greene, "Particulate Impact Mass Spectrometry," presented at the 23rd Annual Meeting of ASMS, Houston Tex., 1975.
11. F. T. Greene, "Mass Spectrometry of Nonvolatile Materials and Solutions y the Particulate Impact Technique," presented at the 24th Annual meeting of the ASMS, San Diego, Calif. 1976.
12. F. T. Greene, "Further Development of Particulate Impact Mass Spectrometry," presented at the 29th Annual Meeting of the ASMS, New York, N.Y. 1980.
13. F. T. Greene, "The Current Status of Particulate Impact Mass Spectrometry," presented at the 29th Annual Meeting of the ASMS, Minneapolis, Minn. 1981.
14. R. C. Willoughby, "Studies with an Aerosol Generation Interface for Liquid Chromatography with Mass Spectrometry," PhD. Thesis, Georgia Institute of Technology, 1983.
15. G. W. Israel and S. K. Friedlander. J. Colloid Interf. Sci. 24, 330 (1967).
16. N. A. Fuchs and A. G. Sutugen. "Highly Dispersed Aerosols". Ann Arbor Science, Ann Arbor (1970).
17. J. W. Jorgenson, S. L. Smith, and M. Novotny, J. Chromatogr., 142, 233 (1977).
18. E. Haakti and T. Nikkari, Acta Chem. Scand. 17, 2565 (1963).
19. R. F. Browner and A. W. Boorn, Anal. Chem. 56/7, 787A (1984).

The above sources are incorporated by reference herein.

SUMMARY OF THE INVENTION

The disclosed invention is a method and apparatus for introducing liquid effluent from process streams, flow injection streams, or liquid chromatographs into analytical devices, such as gas-phase or particle detectors. It is applicable to liquid sample introduction into a variety of analyical devices including mass spectrometers, flame ionization detectors, light scattering detectors, and other apparatuses suitable for determining the nature of analytes in the gaseous or particulate states.

Basic processes occurring in the present device are aerosol generation and desolvation, solute enrichment, and detection of solute by a suitable gas-phase or particle detector.

Aerosol generation with the present invention is obtained by concentric flow of liquid (inner flow) and gas streams (outer flow). The gas is heated by direct contact with a heat source, generally a heated tube that sheathes the gas. The tube is heated by controlled resistive heating of the tube or direct contact of the tube with a cartridge heater. By precisely controlling the flow of gas through the outer tube, the flow of liquid through the inner tube, the dimensions of both tubes, and the power imput for the heat source, the aerosol properties are precisely determined. Heat is conducted across the gaseous medium and therefore the thermal conductivity of the gas is preferred to be high (e.g. hydrogen, helium).

The amount of heat supplied across the gaseous medium to the liquid determines the degree of desolvation or evaporation of solvent that occurs during the aerosol generation process. The gas supply serves two functions in aerosol generation. First, it conducts the heat necessary for desolvation. Second, it confines or sheathes the aerosol particles, preventing the particles from wide dispersion and impacting chamber walls with expansion within an expansion chamber that receives the solvent, the solute and the sheathing gas. The solvent is so received entirely or almost entirely in the gas phase while the solute is in particulate form. The present device requires no desolvation chamber because solvent evaporation takes place entirely inside the inner tube of the aerosol generator.

The controlled aerosol generation and desolvation with the present device effectively separates the solvent from the solute due to the solute being generally less volatile than the solvent. The solvent is thus in the gas-phase and the solute remains in the particulate state.

Once separate in phase, solute enrichment occurs by one of the two methods. The first method of solute enrichment separates the solvent from the solute in a particle beam or momentum separator, where the higher momentum solute particles are carried more efficiently into progressively lower pressure regions separated by skimmer apertures. The present device utilizes either single or dual-stage particle beam pressure reduction. The particle beam configuration in the present device transports most of solute to the low pressure detection region while removing more than ninety-nine percent of the solvent. The second method of solute enrichment, separates solvent from the solute because of mobility of particles compared to gases. The gaseous solvent components of the aerosol having higher mobility interact appreciably with cold surfaces and are trapped on the surfaces, cryotrapping. The solutes, in the particulate state, are carried in the gas flow by a poorly condensable carrier gas such as helium or hydrogen, leaving the solvent vapors behind. A combination of cryotrapping and particle beam solute enrichment is a third alternative.

Detection of enriched solute with the present device is accomplished by a variety of means. One embodiment of the present invention uses particle beam enrichment to direct solute particles into the ion source of the mass spectrometer. The particle beam is intersected by sources which may include primary ion beams, laser beams, discharge plasmas, electron beams, electric fields, or magnetic fields. Under these operating conditions, energy for solute evaporation and ionization is supplied directly t the solute particles during flight. Another embodiment utilizes a target surface to collect the solute particles. The target surface is generally composed of an inert material at a controlled temperature and serves to conduct heat to the particles for obtaining rapid solute vaporization. Once the solute is vaporized, normal gas phase processes provide ionization such as electron impact or chemical ionization. A target surface with collected particles may be bombarded with ions, neutral, or electron beams to create gas-phase ions from the target surface. Alternatively, the solute is collected on a cold target surface for a period of time before heating the target, thus concentrating sample to lower the detection limits. Measurement of power supplied to the target can also be used to determine heat of vaporization.

The use of other gas-phase detectors such as the flame ionization detector (FID) require cryopumping for solute enrichment and hydrogen as the nebulization gas. This embodiment operates with atmospheric pressure or low pressure flames.

The particle beam embodiment is also used with laser scattering or continuum light scattering measurements and functions as a universal liquid chromatography detector.

The invention is illustrated in preferred embodiments in the accompanying drawings.

DETAILED DESCRIPTION OF THE PREFERRED EMBODIMENTS

The present device has three component parts: an aerosol generator 14, a solute enricher, and a solute collector or detector.

Figure 1:
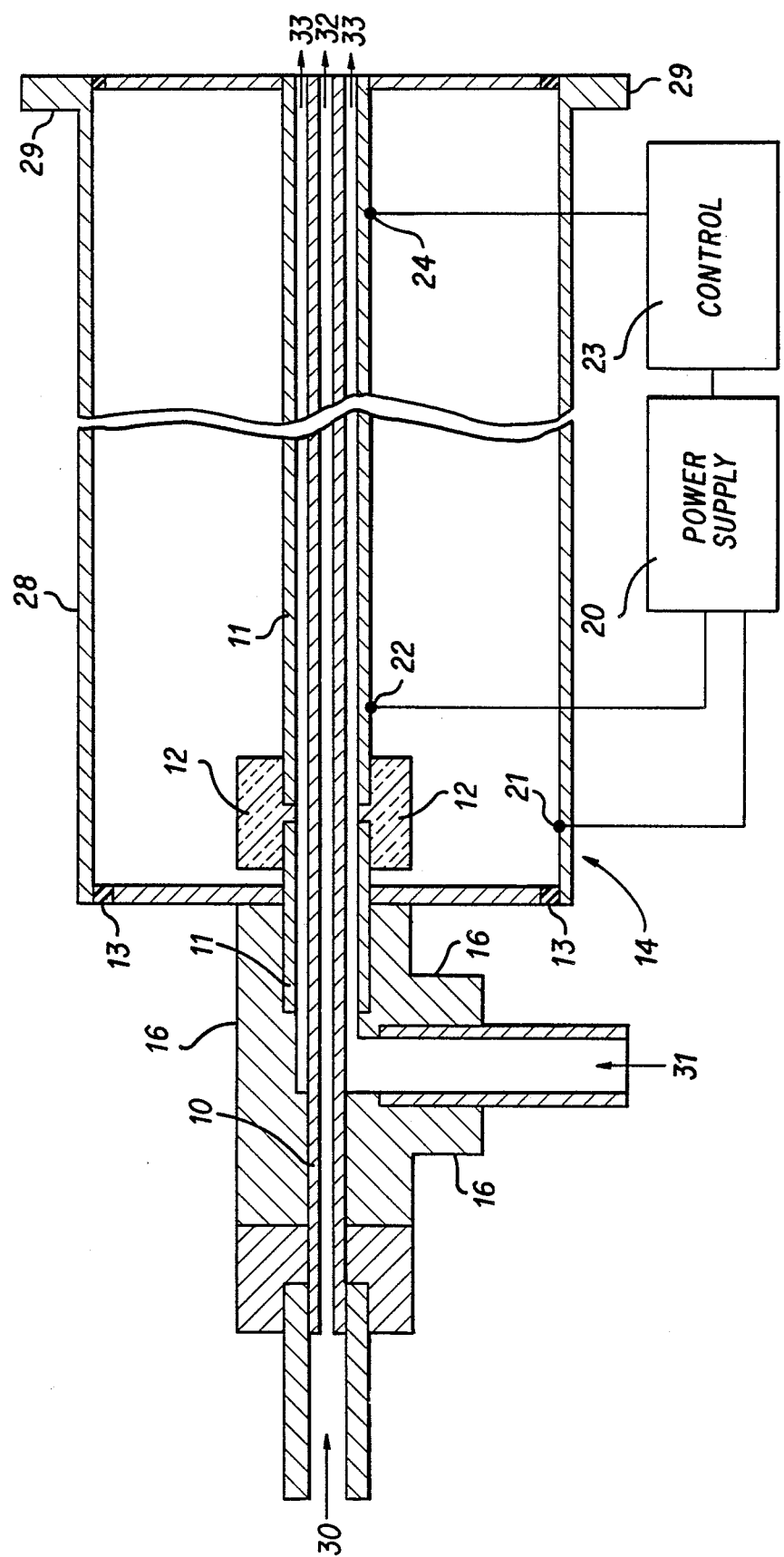
FIG. 1 is a schematic diagram in cross-section of a thermal concentric aerosol generating apparatus with resistive heating of the conductive aerosol generation gas.

The first of these component parts, aerosol generator 14, is described in detail with reference to FIGS. 1 and 2. Flowing into aerosol generator 14 is liquid from supply 30, and gas from supply 31. Gas flows through a conduit comprising a tube 11, and liquid through an inner capillary tube 10. Critical to the operation of aerosol generator 14 is the coaxial supply of heat across the flowing gas medium, between tubes 10 and 11, to flowing liquid in tube 10. The dimensions of the tubes and the flow rates of gas, liquid, and heat determine the properties of the generated aerosol.

The liquid supply 30 for the present aerosol generator is the effluent from liquid process streams, liquid chromatographs, or flow injection streams, the effluent containing dissolved analytes of interest in addition to other less volatile constituents, either present naturally or added purposefully. Fused silica capillary tube 10 functions as a nozzle to confine the flow of the liquid effluent. Tube 10 restricts the flow of liquid resulting in increased linear velocity of the liquid stream as well as increased surface contact per unit volume of liquid with the heated walls of the fused silica capillary. The inner diameter of the fused silica capillary tube 10 has dimensions that are determined by the liquid flow rate requirements for a given application. The minimum inner diameter of tube 10 is determined by the upper pumping pressure limit of liquid supply 30. Liquid flow rate, length, and inner diameter of tube 10 have an effect on the liquid supply pressure. Typical dimensions of the fused silica capillary for liquid flows in the range from 0.1 to 2.0 mL per minute are fifty micrometers inner diameter and two hundred and fifty micrometers outer diameter. Inner diameter dimensions for tube 10 have been successfully tested at ten micrometers, twenty-five micrometers, fifty micrometers, seventy-five micrometers, and one hundred micrometers. The length of the fused silica capillary tubing is that sufficient so that the heat transfer can vaporize the liquid stream before it leaves the tubing. A typical length is twenty centimeters. The maximum length of fused silica capillary tube 10 is determined by the pressure limit of the liquid pumping system.

Gas supply 31 for the aerosol generator 14 comprises a regulated gas source, compressed or self-generated, of a thermally conductive gas or mixture of gases. The coaxial metal capillary tube 11 sheathes the fused silica tube 10 and confines the flow of nebulizer gas supplied from a regulated gas supply 31 and controlled by precision valve 35 (seen in FIG. 3). The inner diameter of the metal capillary tube 11 and the gas flow rate from supply 31 determine the linear velocity of the gas through the metal capillary tube 11 and consequently, the linear velocity of the concentric sheath gas 33 in the aerosol generation process. The concentric gas flow serves two functions in the present device: First, to sheath the aerosol exiting the fused silica capillary tube 10. Second, to serve as a conductive medium for heat transport from the heated outer metal capillary tube 11 to the inner fused silica capillary tube 10.

The heat supply for the present aerosol generator is composed of electrical resistance of the metal capillary tube 11 which causes it to heat. FIG. 1 illustrates means for supplying heat to increase the temperature of capillary tube 11 by passing current through same; the tube being the resistively heated part of the heating circuit. The length, composition, and wall thickness of outer tube 11 determine the power requirements of the heating power supply 20, controlled by heater controller 23. The heating circuit is controlled by maintaining either constant resistance in the circuit or a constant temperature by means of thermocouple feedback 24. The heated outer tube 11 is preferably composed of a pure metal such as nickel or platinum because temperature is proportional to resistance for such pure metals as well as many other pure metals. This relationship permits control of the heat supply or temperature by direct resistance feedback measurement, without the requirement of thermocouple feedback control. The present device may also use thermocouple feedback for heat supply control and resistively heated alloys rather than pure metals. The resistively heating circuit is electrically isolated from ground by appropriate means such as insulators located at 12 and 13. The inner diameter of the heated metal capillary tube 11 is slightly larger than the outer diameter of the inner fused silica capillary tube 10. A typical range for the inner diameter of tube 11 is three hundred to four hundred micrometers. In this range the gas velocity is sufficiently high to entrain the liquid jet or aerosol emerging from the fused silica capillary 10 at position 32. In addition, the interstitial spacing is small enough to allow efficient heat transport across the gas to the fused silica tube 10. There is a portion of capillary tube 11 that is not part of the resistively heated circuit and is connected to the heated portion of tube 11 by the electrically insulated union 12. The region surrounding the outer metal capillary tube 11 conducts heat at a slower rate compared to the rate of heat transport to the inner fused silica tube 10. Consequently, the outer tube is thermally insulated with an air space, a thermal insulating substance, or a vacuum, to ensure heat transport to the flowing liquid stream.

Figure 2:
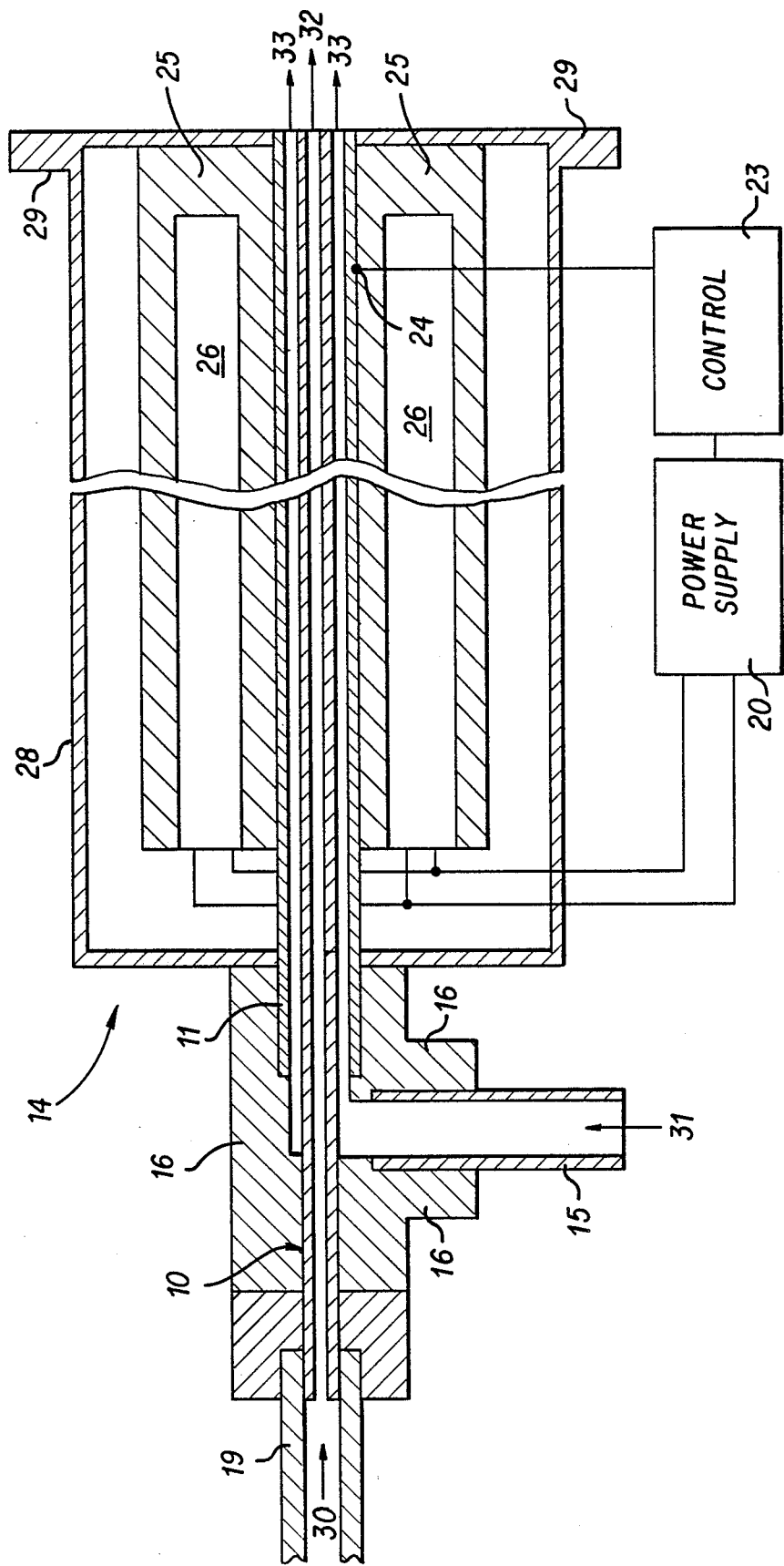
FIG. 2 is a schematic diagram in cross-section of a thermal concentric aerosol generating apparatus with cartridge heating of the conductive aerosol generation gas.

FIG. 2 illustrates an alternative means of heat supply to the metal capillary tube 11 by cartridge heating. Cartridge heaters 26 are inserted into a metal block in thermal contact with the metal capillary tube 11. With cartridge heaters, the means of control for the heater power supply 20 is through thermocouple feedback 24 to controller 23.

The heated portion of the aerosol generator is contained in a protective housing 28 that serves to support the aerosol generator as well as protect the operator from potential burns or electrical shock. The aerosol generator is attached to aerosol expansion chambers via connection 29 which may be a gasket or O-ring seal or both.

The aerosol generation with the present device is obtained by combining the coaxial flow of liquid, gas, and heat in a precisely controlled manner. The aerosol is generated at position 32 and confined along the axis in the direction of flow by sheath gas 33. The coaxial heat transport to the flowing liquid is controlled by electrical feedback circuitry and by the flow of gas between the outer heated metal tube 11 and the inner fused silica capillary tube 10, the gas being the conductive medium across the interstitial space. The thermal conductivity of the gas is a critical parameter in the transport of heat to the inner fused silica tube 10. It is preferred to have the gas supply constitute a high conductivity gas such as hydrogen or helium, but not excluding other less conductive gases or gas mixtures.

The preferred operational conditions for the present aerosol generator depend upon the required aerosol properties for a given application. The range of aerosol properties varies from a pneumaticly nebulized solvent-rich aerosol with relatively large diameter droplets to a thermally nebulized solvent-depleted aerosol with relatively small diameter droplets. The combined pneumatic and thermal nebulization processes yield aerosols that have controlled variation in droplet size, degree of desolvation of droplets, and direction of flow of the generated aerosol generator, as described, functioning to produce solvent-depleted solute particles.

Figure 3:
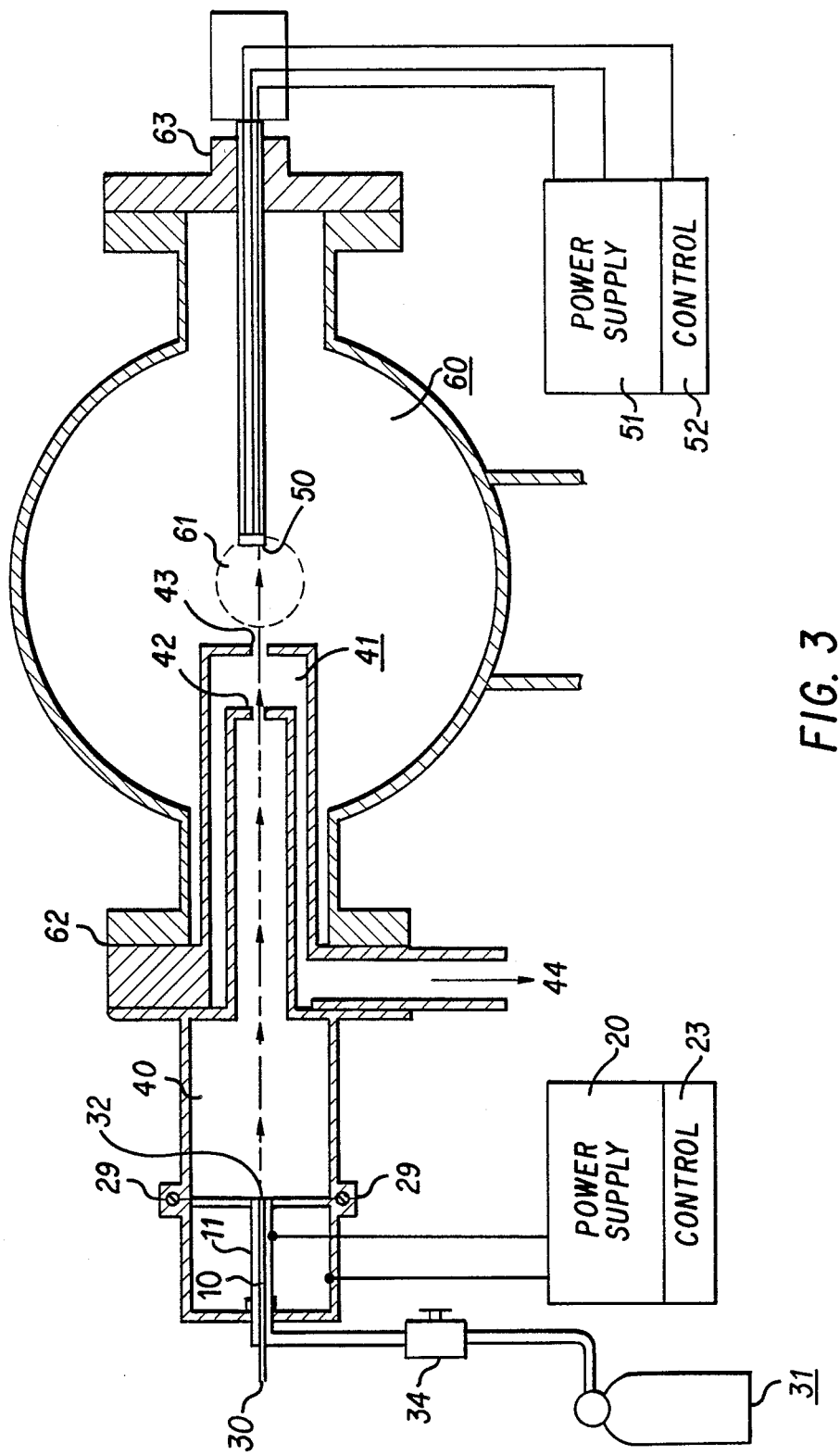
FIG. 3 is a schematic diagram in cross-section of a thermal concentric aerosol generating apparatus and single-stage particle beam solute enrichment to interface with a conventional mass spectrometer ion source chamber flange.
Figure 4:
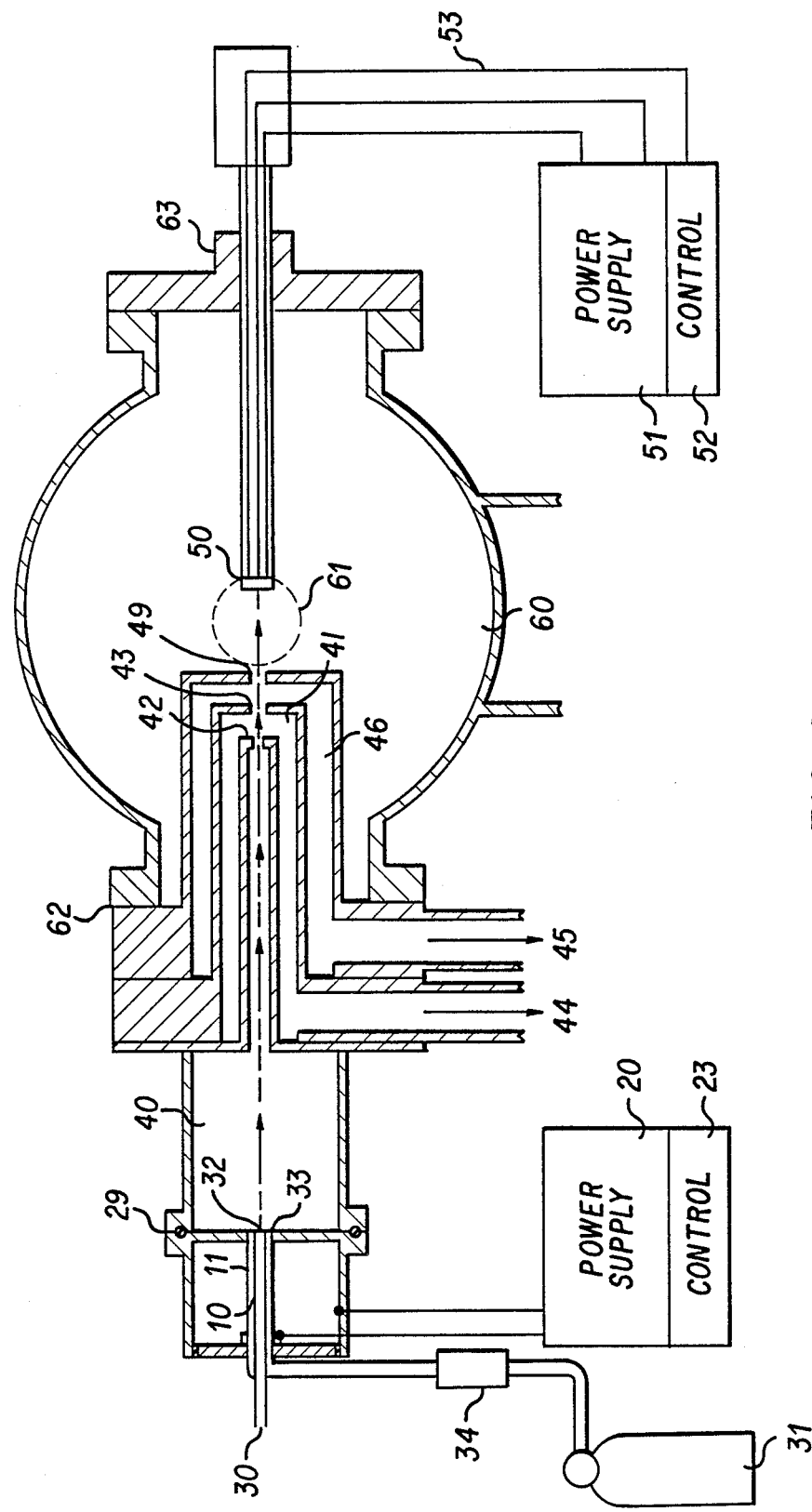
FIG. 4 is a schematic diagram in cross-section of a thermal concentric aerosol generating apparatus and dual-stage particle beam solution enrichment to interface with a conventional mass spectrometer ion source chamber flange.
Figure 5:
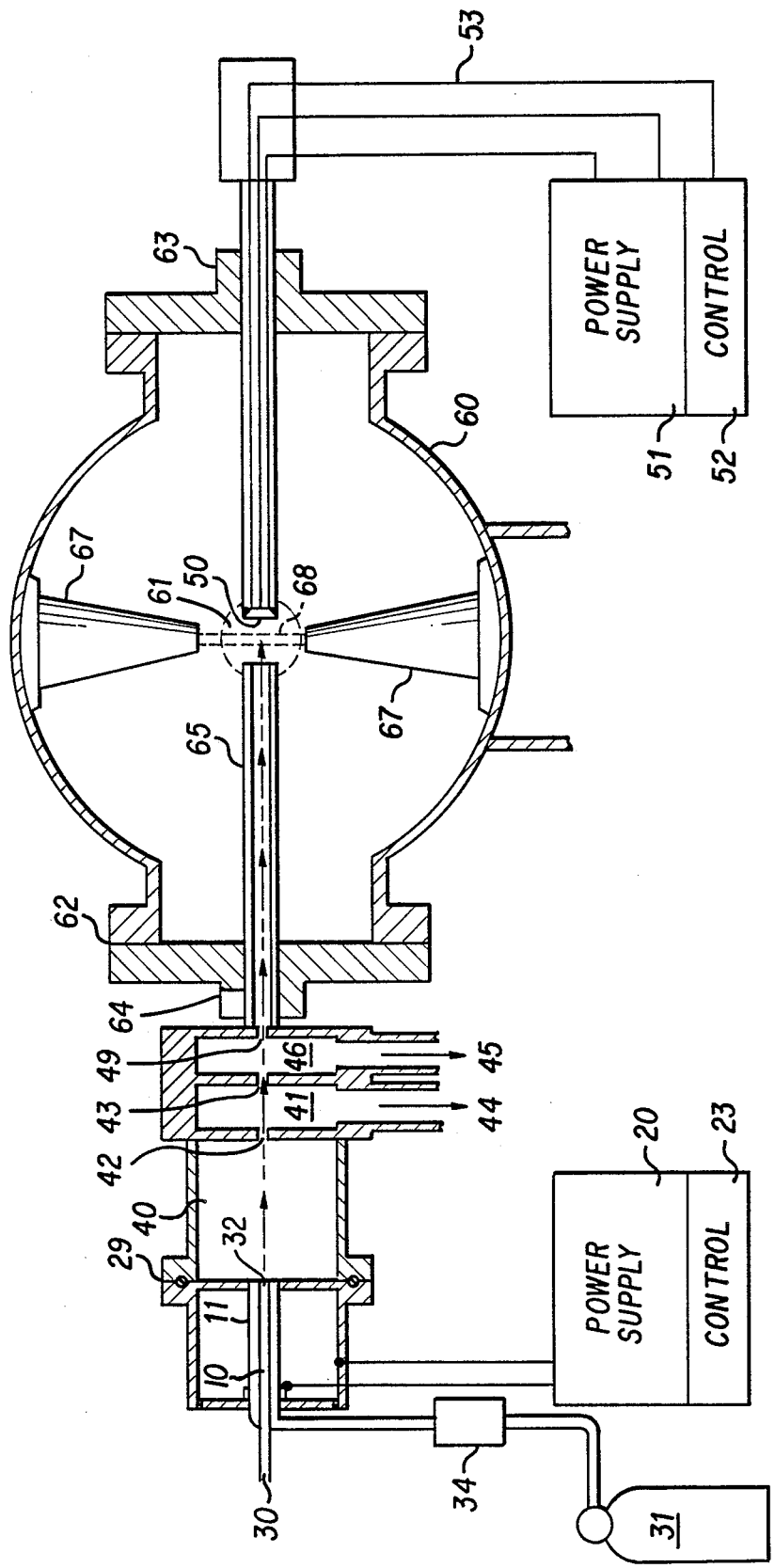
FIG. 5 is a schematic diagram in cross-section of a thermal concentric aerosol generating apparatus and an alternative embodiment of dual-stage particle beam solute enrichment to interface to a conventional mass spectrometer ion source chamber gate valve.
Figure 6:
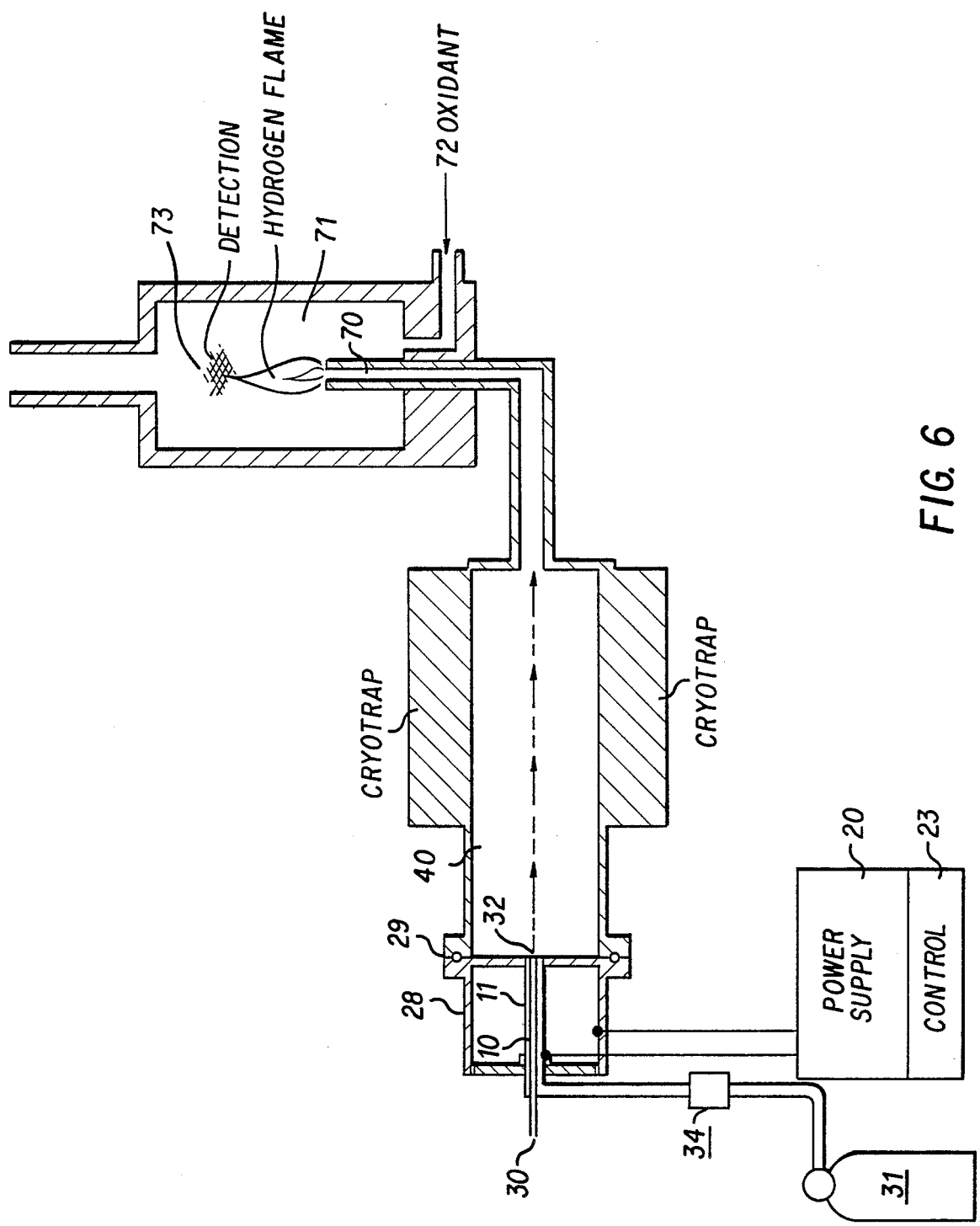
FIG. 6 is a diagramatic view of a thermal concentric aerosol generating apparatus and solvent cryotrapping solute enrichment to interface to a flame ionization detector.

The aerosol generated with the present device requires a solute enrichment step in the embodiments where solute detection is degraded by the presence of proportionately large quantities of solvent. The present device is most generally applicable to effluents where the solutes are less volatile than the associated solvent or soluents. The volatility difference between the solvent and solute results in solute being predominately located in the particulate portion of the aerosol and the solvent predominately located in the vapor portion of the aerosol. FIGS. 3 through 5 illustrate embodiments of the present invention with aerosol generation, particle beam solute enrichment, and mass spectrometric detection. FIG. 6 illustrates an embodiment of the present device with aerosol generation, solvent cryotrapping for solute enrichment, and flame ionization detection. The application of the present device for aerosol generation, solute enrichment, and detection with other modes of detection are not illustrated, but the modifications necessary to attain same will occur to those knowledgeable in the field of liquid sample introduction into gas-phase or particulate detectors from the embodiments disclosed herein.

FIG. 3 depicts the embodiment of the present invention with single stage particle beam solute enrichment. The device is attached to an ion source chamber 60 of a mass spectrometer via a flange vacuum joint 62. The aerosol generator described previously is attached to an aerosol expansion chamber 40 by a sealed joint 29. Expansion chamber 40 provides sufficient space for the high velocity aerosol generated at 32 to be slowed in a viscous flow region and to proceed in the direction indicated by the dashed line and arrows. The pressure in the expansion chamber may vary from near atmospheric pressure down to a pressure adequate to reduce the velocity of the gas, solvent vapor and soluted particles entrained therein sufficiently so that those substances flow in a stream through the expansion chamber without significant loss of sample due to particle impaction on the inner surfaces of the expansion chamber or settling down down to a pressure adequate to reduce the velocity of the gas, solvent vapor and soluted particles entrained therein sufficiently so that those substances flow in a stream through the expansion chamber without significant loss of sample due to particle impaction on the inner surfaces of the expansion chamber or settling, depending upon the mass flow rate from the aerosol generator. The solute particles, sheath gas and solvent vapor are next accelerated through nozzle 42, forming a high velocity aerosol beam along a longitudinal axis between nozzle 42 and skimmer 43. The beam forms due to the pressure drop between expansion chamber 40 and vacuum chamber 41. Vacuum chamber 41 is evacuated by pump 44, generally a large pumping capacity mechanical pump such as a 400 L/min rotary pump. In the region between the axially aligned nozzle 42 and skimmer 43 the solvent vapor and conductive sheath gases from the aerosol expand significantly more rapidly than the solute particles. As a consequence of differential expansion of gases and particles, the particles are highly enriched at the axis of the expanding aerosol beam. The enriched solute particles are sampled into the ion source chamber of the mass spectrometer through skimmer 43. An enriched solute particle beam is formed from the skimmer to the ionization region 61 of the mass spectrometer. The distance between the point where the aerosol beam is formed at nozzle 42 and the ionization region should be kept to a minimum, generally five to ten centimeters.

FIG. 4 illustrates the embodiment of the present invention with two-stage solute particle beam enrichment. As described with respect to FIG. 3, the device is attached to the ion source chamber 60 of a mass spectrometer via flange joint 62. The aerosol generator is attached to the aerosol expansion chamber 40 at sealed joint 29. The aerosol axially expands from the aerosol generator at 32 and proceeds down the axis of expansion chamber 40 in the direction indicated by the dashed line and arrows. The aerosol is accelerated through nozzle 42 forming a high velocity aerosol beam between nozzle 42 and skimmer 43. The aerosol beam is formed due to the pressure drop between the expansion chamber 40 and the first vacuum chamber 41. A second vacuum chamber 46 provides a higher degree of solute enrichment by pumping away additional solvent vapor in the region between skimmer 43 and skimmer 49. The first vacuum chamber 41 is evacuated by pump 44 and the second vacuum chamber is evacuated by pump 45. Pump 44 and 45 have sufficient pumping capability to remove most of the solvent vapor introduced by the aerosol generator. Nozzle 42 and skimmers 43 and 49 are, as before, axially aligned to permit sampling of enriched solute particles into progressively lower pressure regions. The distance between the nozzle 42, where the aerosol beam is formed, and the ionization region 61 is minimized to ensure solute particle transport efficiency. This distance is generally one to ten centimeters.

FIG. 5 illustrates an embodiment of the present invention with two-stage solute particle beam enrichment in an alternative embodiment to that shown in FIG. 4. The device is removable from the ion source chamber 60 of the mass spectrometer through a standard gate valve 64. The insertion probe portion 65 of this device is inserted into gate valve 64 (automatically opening same) so as to be axially aligned with the ionization region 61 of the mass specrometer. The aerosol generator is attached to aerosol expansion chamber 40 at sealed joint 29. The aerosol axially expands from the aerosol generator at 32 and proceeds down the axis of the expansion chamber 40 in the direction indicated by the dashed line and arrows. The aerosol is accelerated through nozzle 42 forming a high velocity aerosol beam between nozzle 42 and skimmer 43. The aerosol beam is formed due to the pressure drop between the expansion chamber 40 and the first vacuum chamber 41. A second vacuum chamber 46 provides a higher degree of solute enrichment by pumping away additional solvent vapor in the region between skimmer 43 and skimmer 49. First vacuum chamber 41 is evacuated by pump 44 and the second vacuum chamber is evacuated by pump 45. Pumps 44 and 45 have sufficient pumping capability to remove most of the solvent vapor and conductive gas introduced by the aerosol generator. Nozzle 42 and skimmers 43 and 49 are, as previously, axially aligned to permit sampling of enriched solute particles into progressively lower pressure regions. The distance between the nozzle 42, where the aerosol beam is formed, and the ionization region 61 is minimized to ensure solute particle transport efficiency; however, with this embodiment, the additional length of the intersection probe 65 is required. This distance is generally in a range of twenty to forty centimeters.

FIG. 5 also discloses optional attachments 67 which may be introduced into ion chamber 60 proximate to and around ionization region 61 for special purposes. For example, attachment 67 may be a laser whereby a laser beam is focused onto the surface of target 61, thus subjecting the beam to photoionization and laser desorption analysis. Also attachment 67 may constitute an electron source for chemical ionization or a high voltage source to ionize particles and molecules by discharge or field ionization. Yet further, attachment 67 may comprise a cryotrap for collecting solvent vapor on cold surfaces while allowing solute particles to pass through the cold trap for subsequent detection. Another form of attachment 67 is apparatus for providing an optical region across the axis of the particle beam for making light scattering measurements on the beam. Attachment 67 may further comprise a support for a moving target, a belt 68 shown in dashed lines, which collects solute particles as a function of time, and wherein apparatus incorporated in attachment 67, or separate apparatus, subsequently locates and analyzes the chromatographic profile so received by surface measurement techniques such as SIMS, infra-red, x-ray, ultraviolet, or visible spectrophotometry scanning or the like such as reflectance or transmittance measurement techniques. Further, belt 68 may collect highly purified solute crystals for subsequent structure analysis. Belt 68 or its equivalent, such as disc or moving strip may be heated for a continuing on-line thermal analysis. In such event, attachment 67 also comprises means for heating the target, controlling such heat, and precisely measuring the thermal energy consumed by evaporation or desorption of solute from the target.

An attachment 67 can constitute apparatus for generating a high energy discharge of sufficient energy to charge surfaces of particles in the beam and thereby enhance ion desorption or particle fission by coulombic repulsion. Attachment 67 may be built-in or, preferably, readily attachable and removable, and plurality of attachments 67 may be disposed in chamber 60 operably proximate the target and region 61 and so that they may be employed alone or in combinations as desired.

The enriched particle beams produced with the embodiments shown in FIGS. 3 to 5 convert the solute particles into gas-phase ions in a similar manner. With each of these devices, the solute particles are collected on a target surface 50. The target surface 50 is a resistively heated surface that supplies thermal energy to minute solute particles to vaporize the solute molecules. The target is inserted through gate valve 63 so that solute vaporization occurs in the ionization region 61 of the mass spectrometer. The temperature of target surface 50 is controlled by controller 52 with thermocouple feedback 53 and power supply 51. The collected solute particles are heated at low temperatures for thermally sensitive compounds and at high temperatures for involatile species and atomization. The operating temperature is for target surface 50 range generally from one hundred degrees to three thousand degrees C. Ionization of the gas-phase solute molecules occurs by conventional ionization processes such as electron impact or chemical ionization.

The ionization processes occurring in the device described with respect to FIGS. 3-5 are not limited to gas-phase ionization. The solute particle beams are also collected on target surface 50 and ionized with conventional surface ionization techniques such as fast atom bombardment, secondary ion mass spectrometry, field desorption, thermal ionization, plasma desorption, and laser desorption as desribed with reference to FIG. 5. These techniques require the introduction of an alternative energy source to the target surface. In addition to surface ionization processes, the present device also permits the introduction of energy to the solute particle beam directly without collection of the particles on a surface prior to ionization. With this embodiment, target surface 50 need not be present. The solute particle beam intercepts, in flight, a primary ion beam, a primary atom beam, a laser beam, or a high field region.

FIG. 6 illustrates the embodiment of the present invention with solvent cryotrapping to provide solute particle enrichment. The aerosol generator is attached to the aerosol expansion chamber 40 at sealed joint 29. The conductive gas used for aerosol generation with this embodiment is hydrogen gas. The aerosol axially expands from the aerosol generator at 32 and proceeds down the axis of the expansion chamber in the direction indicated by the dashed line and arrows. The walls of the expansion chamber 40 are cryogenicly cooled to trap the solvent vapor. The solute particles and hydrogen gas are passed through the expansion chamber more efficiently than the solvent vapor. The enriched solute particles and hydrogen gas are introduced into a burner chamber 71 through inlet 70. Here, the particles are burned in a hydrogen flame and the ions produced in the flame are collected on electrode grid 73. Air or oxygen is introduced into the burner chamber 71 through inlet 72.

The foregoing description of specific embodiments is for clearness of understanding by those skilled in the art and unnecessary limitations should not be unserstood therefrom. The cited prior art patents, literature and patent applications may assist in the understanding of the invention by those skilled in the art as well as those who may desire or need to acquire such an understanding.

Having disclosed my invention, what I claim as new and to be secure by Letters Patent of the United States is:

1. A thermal concentric aerosol generating device for obtaining solvent-depleted solute particles of micron and submicron size in a well defined direction from a liquid sample, the sample containing volatile solvent and less volatile solute, the device comprising:
   a. an inner capillary tube;
   b. a liquid flowing into said tube containing a solvent carrying a solute which is less volatile than said solvent;
   c. heating means associated with said capillary tube that raises the temperature of said solvent while flowing therethrough sufficiently to change the phase of substantially all of said solvent from a liquid to a gas before it emerges from the outlet of said tube;
   d. a conduit surrounding said tube having a gaseous substance flowing therein in the same direction as said solvent;
   e. an expansion chamber receiving the outlets of said conduit and said tube, which are arranged so that said gaseous substance emitted from said conduit's outlet surrounds and guides said solvent gas and said solute in the form of particles away from said outlet of said tube;
   f. an egress from said expansion chamber which is spaced away from said outlets;
   g. the pressure and movement in and through said expansion chamber being such that turbulence within said expansion chamber is minimized and the velocities of said gaseous substance, said gas and said solute particles are approximately the same as they approach and enter said egress and said solute particles are sufficiently guided by said gaseous substance and said gas so that a major part of said solute particles do not impinge on said outlets, the interior walls of said expansion chamber and the interior surfaces of said egress.

2. A thermal concentric aerosol generating device as defined in claim 1, wherein said heating means comprises an electrical circuit with said conduit being the heating element of said circuit, said outer metal tube being composed of a high purity metal having a comparatively high linear relationship between its temperature and resistance.

3. A thermal concentric aerosol generating device as defined in claim 1, wherein said heating means comprises an electrical circuit which includes as a heating element a standard cartridge heater in direct thermal contact with said conduit.

4. A thermal concentric aerosol generating device as defined in claim 1, wherein said expansion chamber is concentric to said outlets and has adequate space for the high velocity gases and particles to have their velocity reduced therein without significant loss of sample due to particle impaction or settling.

5. A thermal concentric aerosol generating device as defined in claim 4, which further includes a supply means for heating said expansion chamber, a control means for controlling said supply means, and a sensing means for monitoring the temperature of said expansion chamber.

6. A thermal concentric aerosol generating device as defined in claim 5, wherein said egress comprises a nozzle restriction at the downstream side of said expansion chamber and coaxial to said inner capillary tube, and wherein the flow of said solute particles therefrom is accelerated through said nozzle forming a high velocity particle beam.

7. A thermal concentric aerosol generating device as defined in claim 6, which further comprises a low pressure chamber downstream from said nozzle, said solute particles, said solvent gas and said gaseous substance enamating at a high velocity from said nozzle to form a beam expanding outwardly along the axis of said nozzle, pumping means removing said gaseous substance and said solvent gas from said beam.

8. A thermal concentric aerosol generating device as defined in claim 7, which further comprises a skimmer located on the downstream side of said low pressure chamber axially aligned with said nozzle, wherein said solute particles in said beam are preferentially sampled over said solvent gas and said gaseous substance by said skimmer to form an enriched solute particle beam.

9. A thermal concentric aerosol generating device as defined in claim 8, which further includes an ion source region of a mass spectrometer axially aligned with said solute particle beam emanating from said skimmer.

10. A thermal concentric aerosol generating device as defined in claim 8, which further includes a second low pressure chamber downstream from said skimmer, said second low pressure chamber being pumped with a second pumping means to provide a pressure drop between said first mentioned low pressure chamber and said second low pressure chamber.

11. A thermal concentric aerosol generating device as defined in claim 10, which further comprises a second skimmer located on the downstream side of said second low pressure chamber axially aligned with said first mentioned skimmer, wherein said solute particles are preferentially sampled over said solvent gas and said gaseous substance successively by said first mentioned and second skimmers to form an enriched solute particle beam.

12. A thermal concentric aerosol generating device as defined in claim 11, which further includes an ion source region of a mass spectrometer axially aligned with said solute particle beam emanating from said second skimmer.

13. A thermal concentric aerosol generating device as defined in claim 7, which further includes means to collect solvent vapor on cold surfaces while allowing solute particles to pass through said cold trap for subsequent detection.

14. A thermal concentric aerosol generating device as defined in claim 1 comprising connective means for being affixed directly to the housing of a mass spectrometer.

15. A thermal concentric aerosol generating device as defined in claim 14 for combination with a mass spectrometer interface including an insertion probe which is readily attachable and removable from the ion source region of said mass spectrometer through a vacuum interlock.

16. A thermal concentric aerosol generating device as defined in claim 15, which further includes a heated target axially aligned to receive said solute particles, said target causing rapid evaporation or flash desorption of said solute particles received by it.

17. A thermal concentric aerosol generating device as defined in claim 16, which further includes control means for controlling the desorption and/or evaporation of solute from the said heated target so that:
  a. said solute particles it receives are desorbed or evaporated as intact molecular species prior to ionization by electron impact or chemical ionization processes,
  b. said received solute particles are thermally ionized from the surface as intact molecular ions, or
  c. said received solute particles are pyrolyzed on the surface of the target to form gas-phase thermal fragments prior to ionization by conventional methods such as electron impact or chemical ionization, and
so that said target's temperature is adjustable for controlled removal of said received solute particles from said target.

18. A thermal concentric aerosol generating device as defined in claim 16, which further includes means for directing a primary ion beam onto the surface of said target so that said received solute molecules are sputtered from the surface of said target to form gas-phase solute ions.

19. A thermal concentric aerosol generating device as defined in claim 16, which further includes means for focusing a laser onto the surface of said target so that a laser desorption or photoionization process occurs.

20. A thermal concentric aerosol generating device as defined in claim 16, which further includes a negative high voltage discharge as a source of electrons for chemical ionization processes and a positive high voltage discharge as a means to ionize particles and molecules by field ionization.

21. A thermal concentric aerosol generating device as defined in claim 14, which further includes an optical region across the axis of said solute particle beam so as to enable light scattering measurements to be made on said solute particle beam.

22. A thermal concentric aerosol generating device as defined in claim 14, which further includes a flat target axially aligned with said salute particle beam so that the particles impact on the surface in a narrow band.

23. A thermal concentric aerosol generating device as defined in claim 14, which further includes a moving target that rastors across the axis of said particle beam and collects solute particles as a function of time so that a target containing a chromatographic profile can subsequently be treated and analyzed using various surface measurement techniques including SIMS, scanning infra-red, ultraviolet, or visible spectrophotometry.

24. A thermal concentric aerosol generating device as defined in claim 23, which further includes a target for collection of said solute particles formed as highly purified solute crystals for subsequent crystal structure analysis.

25. A thermal concentric aerosol generating device as defined in claim 23, which further includes a heated target for collection of sample for on-line thermal analysis, comprising:
  a. means for supplying heat to said target,
  b. means for controlling the supply of heat to said target, and
  c. means for measuring the supply of heat to said target,
permitting the thermal energy consumed by the evaporation or desorption of solute from said target to be precisely measured.

26. A method for generating, transporting, collecting, and analyzing highly dispersed aerosols from solutions containing low volatility solutes for sample introduction into detection devices, concentration of solute, or purification of solute, the method comprising the steps of:
  a. introducing into an inner capillary tube and transmitting therethrough a liquid solvent carrying a solute which is less volatile than the solvent;
  b. introducing and transmitting therethrough a thermally conductive gaseous medium into a conduit concentrically surrounding said capillary tube so that said gaseous medium is flowing in the same direction as said solvent;
  c. heating said gaseous medium sufficiently so hat enough heat energy therefrom is received by said solvent to change said solvent from a liquid to a gaseous phase while flowing through said inner capillary tube;
  d. allowing said gaseous medium and said gaseous solvent with solute particles therein to enter an expansion chamber at high velocities;
  e. decelerating said gaseous medium, said solvent and said solute particles while moving through said expansion chamber sufficiently so that turbulence within said expansion chamber is minimized to a substantial extent while retaining said solute particles concentrated generally in a central path defined by said gaseous medium and said gas flow through said expansion chamber so that a major part of said solute particles are guided by said flowing gas and gaseous medium in a manner to avoid deflection upon emergence from said capillary tube and impingement on the interior walls of said expansion chamber.

27. A method for generating, transporting, collecting and analyzing highly dispersed aerosols as defined in claim 26, which further includes a separation step of pumping of said gaseous solvent non-axially relative to the direction of movement of said solute particles in said expansion chamber.

28. A method for generating, transporting, collecting and analyzing highly dispersed aerosols as defined in claim 27, wherein said solute particles are in the form of an axially aligned particle beam which further includes a pressure reduction step of directing said axial particle beam through at least two skimmers separating differentially pumped chambers.

29. A method for generating transporting, collecting and analyzing highly dispersed aerosols as defined in claim 27, which further includes a step of collecting said solute particles on a target surface for subsequent analysis, the analysis including a selected one or more of the following:
  a. vaporization and ionization for mass spectrometric analysis, or
  b. x-ray diffraction analysis or other crystal or solid particle studying techniques, or
  c. optical analysis including infra-red reflectance or transmittance or other optical techniques using any appropriate wavelength, filter, or monochromater.

30. A method for generating highly dispersed aerosols as defined in claim 26, which further includes a flame ionization step wherein hydrogen being said conductive gas, said conductive gas and said solute particles are burned in the presence of oxygen.

31. A method for vaporizing the enriched solute particles as claimed in claim 28 wherein said solute particle beam is directed through a high energy electrical discharge of sufficient energy to charge the surface of the particles so as to enhance ion desorption or particle fission by coulombic repulsion.

32. A method for vaporizing the enriched solute particles as claimed in claim 28 wherein said solute particle beam is directed to a heated surface with sufficient area to collect said beam and with a sufficient supply of thermal energy to evaporate the solute.

33. A method for vaporizing the enriched solute particles as claimed in claim 28 wherein said solute particle beam is directed onto a heated surface with sufficient surface area to collect said beam where an alternative source of energy causes evaporation, the source of energy comprising a selected one or more of the following:
   a. a laser so that the solute molecules are desorbed from the collector surface using the process known as laser desorption, or
   b. an ion beam so that solute molecules are desorbed from the collector surface using the process known as ion sputtering, or
   c. a high voltage field so that solute molecules are desorbed from the collector surface.

34. A thermal aerosol generating device for obtaining solvent-depleted solute particles of micron or submicron size travelling in a well defined direction from a liquid sample, the sample containing volatile solvent and less volatile solute, the device comprising:
   a. an inner capillary tube;
   b. means for supplying a liquid to flow into said tube containing a solvent which carries a solute which is less volatile than said solvent;
   c. a conduit surrounding said tube and means for introducing into said conduit a thermally conductive gaseous substance which moves in the same direction as said solvent;
   d. heating means to raise the temperature of said gaseous substance and, by thermal conduction through said gaseous substance, the temperature of said solvent and said solute flowing therethrough sufficiently to change the phase of substantially all of said solvent from a liquid to a gas before it emerges from the outlet of said tube;
   e. an expansion chamber receiving the outlets of said conduit and said tube in a manner so that said gaseous substance surrounds and guides said solvent gas and the particles from said solute therein away from the outlet of said tube;
   f. an egress spaced away from said outlets to receive said gaseous substance, said solvent gas and said solute particles as they are emitted from said expansion chamber, the interior of said expansion chamber being maintained at a pressure so that turbulence therein is substantially reduced and the velocities of said gaseous substance, said solute gas and said solvent particles are decreased so that when said gaseous substance, said solvent gas and said solute particles reach said egress, they are moving at approximately the same velocity and said solute particles are concentrated generally centrally in the flow of said gaseous substance and said solvent gas;
   g. at least one stage downstream of said expansion chamber for drawing said gaseous substance and said solvent away from said solute particles; and
   h. an analyzer chamber exposed to a high vacuum for receiving said solute particles downstream of said one stage.

35. A thermal aerosol generating device as defined in claim 34, wherein said heating means comprises an electrical circuit with an outer capillary tube being provided as the heating element of the circuit, said outer capillary tube being composed of high purity metal having a relatively high linear relationship between temperature and resistance.

36. A thermal aerosol generating device as defined in claim 35, wherein said heating means comprises a standard cartridge heater in sufficient thermal contact with said outer metal capillary tube to heat same uniformally.

37. A thermal aerosol generating device as defined in claim 34, which further includes a supply means for heating said expansion chamber, control means for controlling said supply means, and sensing means for monitoring the temperature of the expansion chamber.

38. A thermal aerosol generating device as defined in claim 34, in combination with a mass spectrometer interface directly connected to the housing of a mass spectrometer wherein the efficiency of transport of solute particle beam is enhanced by decreasing the particle beam length.

39. A thermal aerosol generating device as defined in claim 34, in combination with a mass spectrometer interface comprising readily attachable and removable insertion probe for the ion source region of said analyzer chamber which is located in said mass spectrometer through a vacuum interlock.

40. A thermal aerosol generating device as defined in claim 38, which further includes a heated target axially aligned with solute particle beam so that said target causes rapid evaporation or flash desorption of solute particles received on said heated target.

41. A thermal aerosol generating device as defined in claim 40 further comprising a control means for controlling the desorption and/or evaporation of solute from the said heated target so that:
   a. said received solute particles are desorbed or evaporated as intact molecular species prior to ionization by electron impact or chemical ionization process, or
   b. said received solute particles are thermally ionized from the surface as intact molecular ions, as said received solute particles are pyrolyzed on the surface of the target to form gas-phase thermal fragments prior to ionization,
wherein the target temperature can be adjusted for controlled removal of said solute from the said target.

42. A thermal aerosol generating device as defined in claim 40, which further includes means for directing a primary ion beam onto the surface of the said target so that said received solute molecules are sputtered from the surfacer of the target to form gas-phase solute ions.

43. A thermal aerosol generating device as defined in claim 40, which further includes means for focusing a high power laser into the surface of the said target so that laser desorption or photoionization processes may occur.

44. A thermal aerosol generating device as defined in claim 38, which further comprises means for producing a high voltage discharge as an ionization source.

45. A thermal aerosol generating device as defined in claim 34, further comprising an optical region disposed across the axis of a beam formed by said solute particles so as to enable light scattering measurements to be made on said solute particle beam.

46. A thermal aerosol generating device as defined in claim 34, further comprising a flat target axially aligned with a beam formed of said solute particles so that said solute particle beam impacts on said target's surface in a narrow band.

47. A thermal aerosol generating device as defined in claim 39, further comprising a moving target that rastors across the axis of a beam formed of said solute particles and collects solute particles as a function of time so that said target containing a chromatographic profile can be subsequently be treated and analyzed using various surface measurement techniques including SIMS, scanning infra-red, ultraviolet, or visible spectrophotometry.

48. A thermal aerosol generating device as defined in claim 46 wherein said target is provided with heating means for collection of a sample for on-line thermal analysis, said target heating means comprising;
   a. means for supplying heat to the said target,
   b. means for controlling the supply of heat to said target, and
   c. means for measuring the supply of heat to said target, so that the thermal energy consumed by the evaporation or desorption of solute from said target is precisely measured and related to concentration.

49. A thermal aerosol generating device for obtaining solvent-depleted solute particles of micron or submicron size in well defined direction from a liquid sample, the sample containing volatile solvent and less volatile solute, the device comprising:

a. an inner capillary tube which receives a pressurized flow of a liquid solvent carrying a solute which is less volatile than the solvent;

b. a conduit surrounding said capillary tube and means for introducing a gaseous substance to flow therethrough in the same direction as said solvent and said solute;

c. means for providing sufficient heat energy to said capillary tube to increase the temperature of said solvent flowing therethrough sufficiently to change the phase of substantially all of said solvent from a liquid to a gas before it emerges from the outlet of said tube and for raising the temperature of said gaseous substance flowing through said conduit to a temperature higher than that of said solvent gas before it emerges from an opening that surrounds said outlet whereby said gaseous substance surrounds said solvent gas;

d. an expansion chamber receiving said opening of said conduit and said outlet of said tube so that said gaseous substance surrounds and guides said solvent gas and the solute particles away from said outlet of said tube;

e. a higher vacuum stage downstream of said expansion chamber;

f. a passage for the flow of said gaseous substance, said solvent gas and said solute particles from said expansion chamber, the configuration of the interior of said expansion chamber, the deceleration of said gaseous substance, said solvent gas and said solute particles being such as substantially to avoid turbulence therein and to concentrate the flow of said solute particles centrally relative to said gaseous substance and said solvent gas so as to reduce the opportunity of said solute particles being captured by said higher vacuum stage downstream of said expansion chamber wherein said gaseous substance and said solvent gas are stripped away from said solute particles which pass through said higher vacuum stage.

* * * * *